United States Patent [19]

Amaral

[11] Patent Number: 4,604,351
[45] Date of Patent: Aug. 5, 1986

[54] METHOD FOR DETERMINING BACTERIAL SENSITIVITY TO CHEMICAL AGENTS

[75] Inventor: Leonard Amaral, Pound Ridge, N.Y.

[73] Assignee: Bronx Lebanon Hospital, Bronx, N.Y.

[21] Appl. No.: 630,736

[22] Filed: Jul. 13, 1984

Related U.S. Application Data

[62] Division of Ser. No. 554,159, Nov. 22, 1983, abandoned, which is a division of Ser. No. 300,943, Sep. 10, 1981, Pat. No. 4,416,995.

[51] Int. Cl.⁴ .................. C12Q 1/16; C12Q 1/02; C12Q 1/18
[52] U.S. Cl. ..................................... 435/35; 435/29; 435/32
[58] Field of Search ............................ 435/29, 32, 35

[56] References Cited

U.S. PATENT DOCUMENTS

3,509,026  4/1970  Sanders ................................ 435/33
4,035,155  7/1977  Durie et al. ......................... 435/29
4,057,470  11/1977  Schrot ................................ 435/35

Primary Examiner—David M. Naff
Assistant Examiner—Louanne Krawczewicz
Attorney, Agent, or Firm—Kenyon & Kenyon

[57] ABSTRACT

The effect of a chemical on bacterial growth is rapidly determined by culturing a sample of bacteria in the presence of said chemical for a period of time sufficient to obtain detectable bacterial growth. During the culturing period, a labelled nucleotide is added to the growth media and the uptake of said nucleotide is measured and compared to a control.

20 Claims, 2 Drawing Figures

METHOD FOR DETERMINING BACTERIAL SENSITIVITY TO CHEMICAL AGENTS

This is a division of application Ser. No. 554,159 filed Nov. 22, 1983 now abandoned which in turn is a division of application Ser. No. 300,943 filed Sept. 10, 1981, and now U.S. Pat. No. 4,416,995.

This invention is concerned with the determination of bacterial susceptibility to chemical agents. More particularly, this invention is concerned with the determination of the effect of chemical agents on the growth of bacteria. Still more particularly, this invention is concerned with a method for determining bacterial sensitivity to chemical agents, as well as a system, including an automated aparatus, for performing that method.

BACKGROUND OF THE INVENTION

There has long existed a need for rapidly determining the effect of a chemical agent on the growth of bacteria, especially medically significant bacteria, and especially disease causing bacteria. For example, there has long existed a need to rapidly determine the susceptibility of pathogenic bacteria to antibiotics.

It is well known that disease-causing bacteria have varying degrees of susceptibility to bacteriostatic and bactericidal agents (hereinafter referred to as "antibiotics"), and that most effective control of a bacterial infection would be achieved by administering to the patient (human or animal) the most effective antibiotic for the particular bacterial infection in question. However, because of the wide variety of bacteria and antibiotics, this has not been practical for the practicing physician (or veterinarian) because the risk of adverse consequences through selection of the wrong antibiotic is too great. As a consequence, the physician usually selected a broad spectrum antibiotic and hoped that it would be effective against the particular bacteria in question.

Attempts have been made to refine and improve diagnostic procedures for isolating from a patient and characterizing disease-causing bacteria, and ascertaining the most effective antibiotic against that particular bacterial population. However, the procedures developed to date are quite time-consuming, requiring at least 30 hours from collection of a specimen to final report. As a consequence, the practicing physician must still resort to the use of broad-spectrum antibiotics.

The previously known techniques for rapidly determining bacterial susceptibility to antibiotics were based upon optical principles. That is, a specimen was collected, divided into aliquots and subjected to a battery of antibiotics. The resulting samples were then scanned optically, using either turbidometric or light scattering techniques, to ascertain the degree to which a particular antibiotic inhibited the growth of the bacteria, as compared with a control sample. Regardless of the specific optical method employed, such procedures required large samples to provide sufficient bacterial cells to permit optical detection and differentiation, as well as substantial incubation periods during the assay to again generate sufficient numbers of cells to enable accurate comparisons between control and test aliquots. This procedure could consume 48 hours or more. Even with the introduction of automated instruments, which materially reduced the time required to effect analysis of the samples, the procedure still normally required at least 30 hours. Accordingly, although such procedures have been employed in clinical laboratories to follow the course of a bacterial infection in a population, they have not been of practical value to the practicing physician or veterinarian in the diagnosis and treatment of bacterial infections in individual patients.

The known optical techniques are also deficient in another respect. As an aid to more effective treatment, it would be desirable to know not only the most active antibiotic, but also the minimum inhibitory concentration (or "MIC") of the antibiotic against the bacteria in question. However, optical devices cannot be reliably used to determine MIC's because most antibiotics severely affect the morphology of sensitive bacteria during the first four to six hours of exposure. In addition, concentrations of antibiotics close to or slightly below the MIC often have the greatest effect on bacteria morphology. The optical properties of the morphologically altered bacteria and different from those of the untreated control bacteria; and consequently, optical techniques for determining MIC may generate inexact data.

It has been proposed in U.S. Pat. No. 3,676,679 to detect the presence of bacteria in a specimen by culturing the specimen on a culture medium including a $^{14}C$-containing carbon source fermentable to produce gaseous carbon dioxide, such as $^{14}C$-labelled glucose; collecting the gaseous atmosphere over the culture; and measuring its radioactivity. If active bacteria are present in the specimen, radioactively-labelled carbon dioxide will be present in the gaseous atmosphere. However, the patentee contemplated use of this method solely to the detection of the presence of active bacteria. It was not proposed that this procedure be employed to ascertain susceptability to antibiotics.

THE PRESENT INVENTION

It is an object of this invention to provide a new method and apparatus for determining the effect of chemical agents on the growth of bacteria.

It is a further object of this invention to provide a new method and apparatus for rapidly determining the effect of chemical agents on the growth of bacteria.

In a more specific aspect, it is an object of the present invention to provide a novel method and apparatus for determining the susceptibility of bacteria to antibiotics.

In this more specific aspect, it is a further object of the invention to provide a novel method and apparatus for rapidly determining bacterial susceptibility to antibiotics.

Still another object of this invention is the provision of a novel method and apparatus for rapidly and reliably determining the MIC and MBC (Minimum Bactericidal Concentration) of an antibiotic against a bacterial species.

A further object of this invention is to provide a novel method and apparatus for speciating a bacterial population.

SUMMARY OF THE INVENTION

The foregoing and other objects of this invention, which will become evident from the ensuing specification and claims, are achieved by a procedure based upon radioassay techniques, and more specifically the use and detection of radioactively-labelled thymidine, especially tritiated thymidine (or 3H-thymidine).

In accordance with one embodiment of this invention, there is provided a method wherein at least two separate samples of a bacterial population are cultured under controlled conditions in the presence of an aqueous medium including growth factors and radioactively-labelled thymidine, the medium for at least one of such samples (the "test" sample) including a chemical agent whose activity against bacteria is to be determined, and the medium for at least one other of such samples (the "control" sample) not including such chemical agent; determining the uptake of such radioactively-labelled thymidine by the "test" sample and the "control" sample; and comparing the respective thymidine uptakes of the two samples.

With specific reference to the application of this invention to the determination of the susceptibility of bacteria to antibiotics (or potential antibiotics), the present invention contemplates: (1) division of a bacterial population into at least two subpopulations; (2) culturing the subpopulations in the presence of a growth-supporting medium and radioactively-labelled thymidine, at least one of said subpopulations including an antibiotic (or potential antibiotic) and at least another of such subpopulation being free of such antibiotic (or potential antibiotic); (3) measuring the radioactivity of each of said subpopulations; and (4) comparing the radioactivity of each of said subpopulations.

The process of the present invention is based upon the concept that bacterial growth must be preceded by the synthesis of bacterial DNA. Therefore, the most sensitive and most rapid measure of the effect of a specific chemical on the growth of bacteria is the effect of that chemical on the synthesis of DNA by the bacteria. Thus, if a chemical is an antibiotic, i.e., it inhibits or prevents bacterial growth, its effect is manifested by inhibition or prevention of bacterial synthesis of DNA. Conversely, if a chemical supports or stimulates bacterial growth, its effect is manifested by increased DNA synthesis. It is a further premise of this invention that changes in DNA synthesis may be accurately ascertained, and more importantly, they may be ascertained before changes in the growth of bacterial population may be accurately determined.

The process of the present invention is also based upon the fact that, of the natural nucleotides comprising DNA, thymidine is the only one specific to DNA. That is, DNA is comprised of four nucleotides, of which thymidine is the only one which is not a component of RNA. Thus, the rate of uptake of thymidine is a specific indicator of the rate of DNA synthesis, whereas use of other natural nucleotides would not be specific for DNA. It is also possible to employ thymidine analogs which participate in DNA synthesis in a manner similar to thymidine; however, for practical purposes, thymidine is readily available and for that reason, it is preferred.

In a second embodiment of this invention, there is provided apparatus for performing the process of this invention, which apparatus comprises means for containing a first (control) mixture of a growth-supporting medium, bacteria and radioactively-labelled thymidine; means for containing a second test mixture of growth-supporting medium, bacteria, radioactively-labelled thyidine and a selected chemical agent; means for incubating such first and second mixtures for a selected period of time; means for separating the bacteria from each of such first and second mixutres; and means for determining the radioactivity of the bacteria separated from such first and second mixtures. In a particularly preferred form of the apparatus, there is provided an automated apparatus including automated means for dispensing and mixing components of the control and test mixtures; means for incubating such samples at a predetermined time and temperature; means for transferring such samples to such incubation means; means for separating bacteria from such samples; means for transferring such samples from said incubator means to said separated means; and means for determining the radioactivity of the thus-separated bacteria.

In still another aspect of this invention, there is provided a novel container employed in the apparatus of this invention. The container essentially comprises an open-ended tubular top portion and an open-ended, conical bottom portion, and having disposed therein means adapted to retain a bacterial culture in the tubular top portion under normal ambient conditions, but which allows the liquid portion, but not the solid (i.e., bacteria) portion of such culture to pass through under the influence of a pressure differential across such retaining means.

DETAILED DESCRIPTION OF THE INVENTION

As is noted above, the present invention is based upon the use of radioactively-labelled thymidine or a radioactively-labelled analog of thymidine to measure the rate of growth of bacteria. The thymidine (or thymidine analog) may be radioactively labelled in any suitable fashion. For example, the thymidine can contain radioactive isotopes of such elements as hydrogen, carbon, phosphorus, nitrogen, oxygen or iodine, for example, tritium, carbon-14, phosphorus-32, iodine-125 or iodine-131. Isotopes such as $^{125}I$ and $^{131}I$, which are gamma-ray emitters, are less desirable than beta-ray emitters for reasons of safety. Radioactive isotopes of phosphorus, oxygen and nitrogen, although technically feasible, are not desirable due to their expense and inability to impart high specific activity to the labelled thymidine. Consequently, tritium and $^{14}C$ are the preferred isotopes. Carbon-14 is desirable because it permits the use of a radioactively-labelled thymidine with the highest specific activity. However, tritiated thymidine is readily available at less cost than $^{14}C$-labelled thymidine. Hence, tritiated thymidine is preferred based upon economic considerations.

When employing tritiated thymidine, it is desired that it have a specific activity in excess of 6 Curies per millimole (Ci/mmole). Tritiated thymidine having a specific activity of 6 Ci/mmole is commercially available, and is satisfactory for use in this invention. Tritiated thymidine having a specific activity of at least 20 curies per millimole is desired in some circumstances. High specific activity tritiated thymidine (40–60 Ci/mmole) has been reported by Durie et al. in U.S. Pat. No. 4,035,155, as useful in high speed autoscintillation radiography, and may be employed in the practice of this invention as well.

As has been noted above, the technique of this invention has value in ascertaining the activity of chemical agents (i.e., antibiotics and potential antibiotics) against bacteria. More particularly, the technique of this invention is useful in the clinical determination of bacterial susceptibility to antibiotics. When employed for this purpose, a specimen to be subjected to analysis, for example blood, urine, a swab, or a sample of bacteria infested water, is obtained, and if not already in the form of an aqueous bacterial suspension, it is suspended in an aqueous medium prior to being subjected to the process of this invention. The size of the sample is not highly critical, provided a sufficient number of bacteria are obtained to permit the intended procedures to be performed. Further, the number of bacteria present in the aqueous suspension are not narrowly critical, provided a sufficient number of bacteria are present for the procedure of this invention to detect differences between test and control samples. However, the time required to perform the analysis can be reduced as the concentration of bacteria increases. It has been found, as a general rule, that the aqueous bacterial suspension should contain at least about $10^4$ cells per milliliter and concentrations of from about $10^5$ to about $10^{10}$ cells/ml are generally useful. Applicant has worked with concentrations of the order of $5 \times 10^8$ to facilitate comparison of the results of this method with those of the known Kirby-Bauer technique. If the specimen has too low a cell concentration, it may be concentrated by known techniques, such as centrifugation or by culturing.

The aqueous suspension may contain a single bacteria species, or a mixture of bacteria. If the initial specimen comprises several different species of bacteria, it may be desirable to culture the specimen overnight to obtain individual bacterial colonies which then may be separately employed in the process of this invention.

The aqueous bacterial suspension which is to be subjected to the analytical technique of this invention desirably includes nutrients capable of supporting bacterial growth. Consequently, the bacteria are desirably suspended in liquid culture media, in particular culture media which are known as "complete" culture media. Such liquid culture media are well known, and will not be further discussed, except to note that applicant has employed trypticase soy broth, and found it suitable for use in accordance with this invention.

The first step of the process of this invention comprises adding one portion of the sample to a complete liquid culture medium containing the chemical whose activity is to be determined, and adding another portion of the sample to the culture medium without the chemical to serve as a control. The culture medium is desirably the same as that used in preparing the initial sample, e.g., trypticase soy broth. The size of the resulting mixtures is not highly critical, provided there is sufficient material in the test and control media to permit one to obtain detectable growth in at least the control sample. On the other hand, it is desirable to minimize the size of the sample to conserve materials. In general, analytical samples having a volume in the range of from about 250 microliters ($\mu l$) up to about 1 to 2 milliliters are useful. In forming such a sample, the bacterial suspension is preferably added to the culture medium contained in a suitable container, thereby diluting the bacterial suspension by a factor of about 10. For example, a 100 $\mu l$ sample of bacteria suspension is diluted with about 1 ml of liquid culture medium to make up the analytical specimen. Thus, the concentration of cells in each analytical sample is at least about $10^3$ cells per milliliter, and preferably in the range of $10^4$ to $10^9$ per milliliter.

The test sample also contains the chemical whose activity is to be determined. The chemical may be a known antibiotic when the test is employed to ascertain susceptibility of the bacteria to antibiotics, or it may be an experimental chemical whose antibacterial activity may be under investigation. The chemical may also be one capable of stimulating bacterial growth, in which case it can be used in procedures for speciating an unknown bacterial sample.

After forming the test and control specimens, they are incubated under conditions suitable for sustaining bacterial growth. As a general rule, this means incubation at a temperature of from about 35° to about 38° C., although higher or lower temperatures may be required for certain bacteria. The period of incubation is that period sufficient to obtain detectable growth, which will differ depending upon factors such as bacterial species, concentration, etc. That is, different bacterial species have different growth rates. Further, differences in growth rates between test and control specimens are more readily determined if high cell concentrations (e.g., $10^6$ to $10^{10}$ cells mml) or high concentrations of radioactively-labelled thymidine are present in the samples. In general, however, the incubation should be at least about one-half hour. If the process of this invention is to be of significant value in rapid clinical determination of antibiotic susceptibility of bacteria, the conditions should be such that the incubation period is not greater than $2\frac{1}{2}$ hours. Of course, if rapid determinations are not desired, still longer incubation periods are permissible.

After incubation of the test and control specimens for a period of time, the radioactively-labelled thymidine is added to both specimens and the resulting samples are then incubated for an additional period of time. As is noted above, the bacteria in both samples will incorporate the labelled thymidine into newly synthesized DNA, and the differences in the rates of bacterial uptake of the labelled thymidine in the control and test specimens is a measure of the effect of the test chemical on bacterial growth. That is, a slower rate of uptake by bacteria in the test specimen, as compared to the control, results if the chemical is an effective antibiotic. Conversely, increased thymidine uptake in the test specimen results if the chemical stimulates bacterial growth.

It is desired that the time of addition of the radioactively-labelled thymidine be such that it maximizes the detectable differences between test and control specimens. Accordingly, the addition of thymidine should be delayed until the last possible moment. If the thymidine is added early in the cycle, at a point in time before the test chemical has had a significant effect on the test bacteria, i.e., before there has been an opportunity for significant differences in the sizes of the respective bacterial populations to occur, the measurement of differences will be more difficult. On the other hand, there must be a sufficient time period after addition of the labelled thymidine to allow a measurable difference in thymidine uptake to occur. As a general rule, the incubation period following addition of labelled thymidine should be in the range of from about 5 to about 25 minutes, and preferably is of the order of about 15 minutes.

Following incubation in the presence of thymidine, both control and test samples are analyzed to determine the the respective thymidine uptakes of the bacteria. Methods for making such determinations are known, and are not a feature of this invention. For example, the reduction in concentration of radioactive thymidine in the test and control aqueous media can be measured, or the amount of radioactive thymidine present in the test and control bacteria can be measured, with the latter being preferred.

Further, the technique for determining bacterial content of radioactively-labelled thymidine can be any suitable procedure, the particular procedure not forming a part of the invention. In general, however, the bacteria must be separated from the aqueous medium and before the level of radioactivity can be determined. For example, the sample can be centrifuged and the supernatant be decanted to leave the bacteria which, after washing, are tested for radioactive content. In such a case, the precipitated bacteria preferably are resuspended in an aqueous medium, a scintillant is added, and the degree of radiation is determined with a scintillation counter. Another, and preferred, procedure comprises adding a precipitating agent, such as 10% trichloroacetic acid, and filtering the resulting mixture to deposit the precipitated bacteria on the filter medium. The filter medium, after washing and drying, is immersed in a liquid scintillant, and the level of radioactivity is again measured with a scintillation counter.

The measured radioactivities of the test and control samples are then compared and the difference, if any, is determined. In general, it is desired to repeat each analysis a sufficient number of times to obtain statistically significant results. The number of repeats will depend upon the degree of precision desired, but ordinarily three repeats are sufficient for most purposes.

When the process of this invention is employed to ascertain susceptibility of a bacterial population to known antibiotics to enable rapid diagnosis and treatment, the procedure is run using a battery of antibiotics known to be effective against pathogenic bacteria. For this purpose, however, antibiotics known to inhibit bacterial synthesis of thymidine cannot be employed. This is because, if such antibiotics are present, bacterial uptake of exogenous thymidine is stimulated, and a false "negative" response will be obtained. In addition, it has been found that predictive responses cannot be obtained with streptomycin and tetracycline. Although both inhibit bacterial growth at the outset, bacterial growth will occur over time.

When the technique of this invention is employed for determining bacterial susceptibility to antibiotics, it may be used to determine minimum inhibition concentrations (MIC) of active antibiotics. For this purpose, the concentration of the test antibiotic is varied in a series of test specimens to generate data permitting calculation of the MIC of the antibiotic.

The method of this invention also is useful in speciating unknown bacteria. That is, if the effects of a battery of different chemicals on various bacteria are known, and where the pattern of the effects varies from bacterial species to bacterial species, an unknown bacteria can be subjected to the battery of chemicals, the pattern of activity determined and, based upon that pattern, the species of the unknown bacteria rapidly determined. For such purposes, chemicals having no effect, or which even stimulate bacterial growth, may be employed.

In the second embodiment of this invention, there is provided apparatus for performing the process of this invention. The apparatus comprises, in combination:

(1) a plurality of containers for the test and control samples comprising aqueous bacterial suspension to be subjected to the process of the invention;

(2) means for forming such test and control samples and changing such samples to such containers;

(3) means for incubating the samples while in such containers;

(4) means for separating bacteria from the liquid pulse of such suspension; and (5) means for determining the radioactive content of the thus-separated bacteria.

The container employed in the apparatus of this invention can be any container, such as a test tube, capable of holding the test and control samples. In accordance with the preferred form of the apparatus of this invention, the container should have a capacity of from about 250 $\mu$l to about 2 ml of sample. As is discussed in greater detail below, a further embodiment of this invention is concerned with a novel container especially adapted of use in the method and apparatus of this invention.

The means for forming and dispensing the test and control samples includes individual storage means for the growth-supporting medium, for a bacterial suspension, for radioactively-labelled thymidine and for a selected chemical agent whose activity is to be ascertained; means for mixing the growth-supporting medium, bacterial suspension, radioactively-labelled thymidine and, for the test sample, the selected test chemical; and means for dispensing the resulting mixture into the containers. In a preferred form, the means for forming and dispensing the test and control samples comprises means for premixing predetermined quantities of the bacterial suspension and growth-supporting or culture medium, and delivering such quantities to be mixed under the control of a photometer. The photometer, which may be of a programmable type, adjusts the optical density of the sample containing the bacterial suspension and the culture media, in accordance with a predetermined optical density. The resulting mixture is then mixed with radioactively-labelled thymidine and, in the test sample, the test chemical. The mixing and dispensing means includes further means for mixing the resulting mixture of bacterial suspension and culture medium with the thymidine and test chemical and dispensing the resulting mixture to the culture containers. In a preferred embodiment the dispensing and mixing apparatus is adapted to dispense, in sequence, the mixture of the bacterial suspension and growth-control medium, the radioactively-labelled thymidine and the test chemical.

In a further embodiment of this invention, the mixing and dispensing means includes storage means for other materials employed in the process of this invention, such as storage means for precipatants for bacteria (e.g., trichloroacetic acid), and washing media, and means for dispensing these materials to the culture tubes.

In a particularly preferred form, the dispensing means is automated so as to dispense predetermined aliquots of the various materials in a predetermined timed sequence under the control of a master computer.

The dispenser employed in the apparatus receives the fluids, including antibiotic solutions, tritiated thymidine, trichloroacetic acid, and a washing solution. The timed and sequential aliquots of these fluids are provided at an outlet of the automatic dispenser, for discharge into culture tubes.

The culture tubes are then incubated in suitable incubating means. It is preferred that the incubating means include means for transporting culture tubes to a station including the dispensing means, when the materials are charged to the culture tubes, while maintaining the culture tubes and their contents at a predetermined incubation temperature. In a preferred form of the invention, such transport means comprises a rotating turntable. In an automated embodiment, the turntable is programmed to present culture tubes to the dispensing station in accordance with the predetermined timed and sequential schedule for discharge of materials from the automated dispenser.

In a further aspect of the invention, the transport means is provided with means to agitate the culture containers. Such agitation means may be a vibrator device which operates during the incubation period and at other predeterminable times to ensure homogeneous mixing of the culture tube contents.

The apparatus of this invention further comprises means for separating bacteria from the liquid portion of the samples. In a preferred form, suitable means comprise a filter, such as a millipore filter, which permits liquid to pass through the filter while retaining bacteria. In an especially preferred aspect of this invention, such filter means are disposed within the culture tube, as is discussed more fully below.

Finally, the apparatus of this invention comprises means for ascertaining the radioactive content of the bacteria samples. In a preferred embodiment, such means comprise means for dispensing a liquid scintillant, means for mixing said scintillant with bacteria, and a scintillation counter.

A particularly preferred form of the apparatus of this invention will now be described with reference to the drawings.

Figures 1, 2:
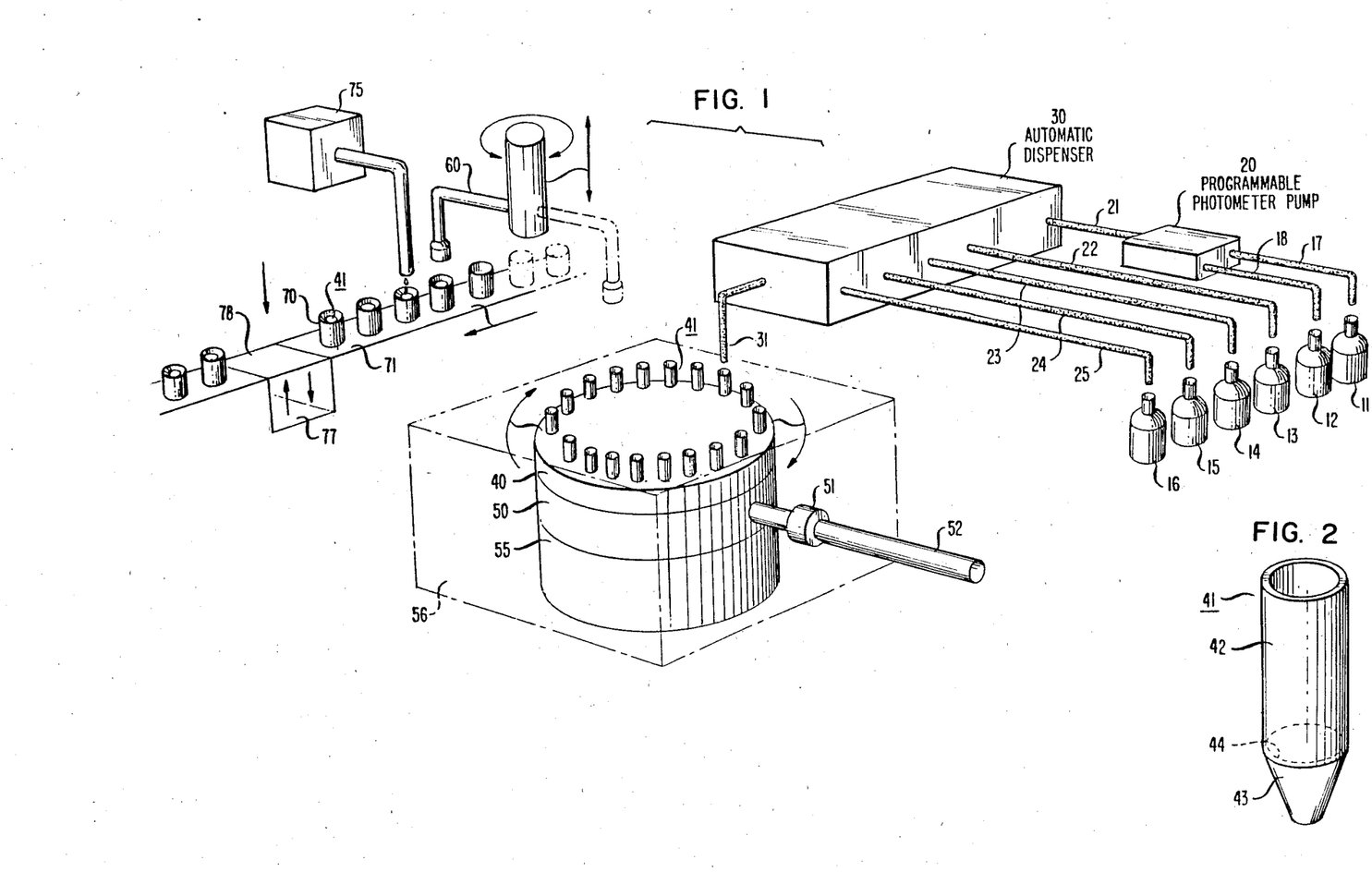
FIG. 1 is a schematic drawing illustrating one form of apparatus of the present invention.
FIG. 2 is a drawing illustrating the container of this invention.

With respect to FIG. 1, there is shown a schematic representation of an arrangement of components and subsystems for determining the sensitivity of bacteria to predetermined chemical agents employing the method of this invention. Supply vessels 11, 12, 13, 14, 15, and 16, each contain respective substances which are desired to be employed in the process of the invention. In the specific illustrative embodiment, vessel 11 contains an aqueous bacterial suspension which is to be subjected to an analytical technique in accordance with the principles of this invention; vessel 12 contains a liquid culture medium of a known type, illustratively trypticase soy broth; vessel 13 contains a chemical agent, which may be an antibiotic, the effects of which upon the growth rate of the bacteria in vessel 11 are desired to be determined; vessel 14 contains a supply of radioactively-labelled thymidine or thymidine analog, preferably tritiated thymidine (3H-thymidine); vessel 15 contains trichloroacetic acid; and vessel 16 contains a washing solution.

Vessels 11 and 12 are coupled by respective lines 17 and 18 to a unit 20 which contains a pump and a photometer, preferably a programmable photometer. The pump of unit 20 draws fluids from vessels 11 and 12, the fluids being combined in accordance with a predetermined optical density determined by the photometer. Thus, unit 20 provides at output line 21 a mixture of bacteria from vessel 11 and a culture medium, such as trypticase soy broth, from vessel 12. Line 21 is coupled to an input of an automatic dispenser 30 which receives at further inputs the fluids of vessels 13, 14, 15, and 16 via lines 22, 23, 24, and 25, respectively. The automatic dispenser is provided with an outlet 31 for dispensing timed and sequential aliquots of the fluids from lines 21 through 25.

A programmable turntable 40 is provided with a plurality of stations, each station containing a culture tube 41. As is shown in FIG. 2, each tube 41 has a cylindrically shaped upper portion 42 and a conical lower portion 43. Both ends of tube 41 are open. A fixed millipore filter 44 is arranged within tube 41 so that any fluid introduced into upper portion 42 and which is transferred to lower portion 43 passes through filter 44. The tube may be constructed of any suitable material; however, use of inert thermoplastic materials, such as polyethylene or polypropylene is preferred.

Programmable turntable 40 is arranged on a vacuum manifold 50 which is serially coupled to a vacuum pump which produces a negative pressure at the lower end of tubes 41 at a predetermined time, so as to cause the fluids present in the upper portions of the tube 41 to be drawn through the fixed millipore filter 44. Manifold 50 is provided with inlets (not shown) for engaging conical portions 43 of tubes 41. Thus, after a fluid mixture from outlet 31 of dispenser 30 is deposited in upper portion 42 of tubes 41, vacuum manifold 50, which is provided with a vacuum pump 51, exerts a negative pressure in lower portion 43 of the polyethylene tubes, so as to cause the fluid contained in upper portion 42 to pass through filter 44, into conical section 43, and into the vacuum manifold 50. The fluid so drawn is conducted to a waste drain 52.

In some embodiments of the invention, programmable turntable 40 may be provided with a programmable vibrator 55 for producing vibratory motion of the turntable, polyethylene tubes, and their fluid contents. Vibrator 55 serves to agitate and thereby throughly mix the fluids comprising the cultures contained in the polyethylene tubes. In addition, the programmable turntable is provided with an incubator 56 which maintains a predetermined temperature for the fluids within tubes 41, during predetermined incubation intervals.

After separation of liquid from bacteria, a rotating transfer armlift arrangement 60 removes each tube 41 from programmable turntable 40 and inserts each into a respective scintillation vial 70. A plurality of the scintillation vials are arranged on an automated conveyor system 71. The tubes which are contained within the scintillation vials receive predetermined doses of scintillation fluid from a dispenser 75 of scintillation fluid. After receiving the scintillation fluid, the scintillation vials are conveyed to a scintillation counter 77 which then determines the radioactivity of the culture within the polyethylene tubes. In a preferred embodiment, the scintillation vials are lowered into a well of scintillation counter 77 by an elevator 78, which returns the scintillation vials to the conveyor after the radiation measurement is taken.

In a highly automated embodiment of the invention, programmable photometer 20, automatic dispenser 30, programmable turntable 40, vacuum pump 51, vibrator 55, incubator 56, transfer lift arm 60, conveyor 71, dispenser of scintillation fluid 75, and radioactivity counter 77 may all be under the control of a master computer (not shown). In addition to controlling the operation of the inventive system, the master computer may be programmed to collate data obtained from the radiation counter, receive patient information, and with a stored computer file, identify the bacteria contained in vessel 11 and complete all necessary items pertinent to a final report.

As previously indicated, the first step to be executed by the inventive system is the combination of the aqueous bacterial suspension contained in vessel 11, which may already contain trypticase soy broth, with a further amount of trypticase soy broth from vessel 12 so as to provide a mixture having a predetermined optical density determined by the photometer in unit 20. This mixture is conducted through line 21 and through dispenser 30 so as to be deposited in polyethylene tubes 41 on the programmable turntable. The amount of the mixture deposited in the polyethylene tubes is not highly critical, provided there is sufficient material in the test and control samples to permit one to obtain a detectable measure of growth in at least the control sample. It is, however, desirable to minimize the size of the samples so as to conserve materials. In general, analytical samples having a volume in the range of approximately 250 microliters up to approximately 2 milliliters are useful. In one practicable embodiment, the bacterial suspension in vessel 11 is diluted with the culture medium in vessel 12 by a factor of approximately 10. For example, a 100 microliter sample of bacterial suspension is diluted with approximately 1 milliliter of liquid culture medium to make up the analytical specimen. Thus, the concentration of bacterial cells in each analytical sample is approximately $10^3$ cells per milliliter, and preferable within the range of $10^4$ to $10^9$ bacterial cells per milliliter.

Some of the samples in tubes 41 will be converted to test samples by depositing therein a predetermined quantity of the chemical agent contained in vessel 13. As stated, the chemical agent may be a known antibiotic in situations where the inventive equipment is employed to ascertain susceptibility of the bacteria to antibiotics, or it may be an experimental chemical, the antibacterial activity of which may be under investigation. Alternatively, the chemical agent may be capable of stimulating bacterial growth, thereby permitting the system to be used for speciating an unknown bacterial sample.

After the test and control samples are deposited in the polyethylene tubes, the contents may be agitated by vibrator 55 and incubated under conditions suitable for sustaining bacterial growth. As a general rule, such incubation is performed at a temperature of from approximately 35° C. to about 38° C., although higher or lower temperature may be required for certain bacteria. The period of incubation is selected to be sufficient to obtain detectable growth in the control samples. Of course, the amount of growth will differ depending upon factors such as bacterial species, concentration, etc. It should be noted that differences between the growth rates of the test and control samples are more readily determined with relatively high cell concentrations, illustratively $10^6$ to $10^{10}$ cells per milliliter. In general, the incubation should be at least approximately one-half hour in duration, and generally not greater than two and one-half hours. In situations where rapid determinations are not necessary, longer incubation periods are permissible.

After incubation of the test and control specimens has been performed for a period of time, radioactively-labelled thymidine, illustratively tritiated thymidine from vessel 14, is added to both specimens, and the resulting samples are then incubated for an additional period of time. As previously noted, the bacteria in both samples will incorporate the labelled thymidine into newly synthesized DNA, and the difference in the rate of bacterial uptake of the thymidine in the control and test specimens is a measure of the effect of the test chemical on bacterial growth. Thus, a slower rate of uptake by bacteria in the test specimen, as compared to the control specimen, will result if the chemical is an effective antibiotic. Conversely, increased thymidine uptake in the test specimen results if the chemical agent stimulates bacterial growth.

Following the incubation in the presence of thymidine, the amount of radioactive thymidine present in the test and control bacteria is measured. In general, the bacteria must be separated from the aqueous medium before the level of radioactivity can be determined. A precipitating agent, such as 10% trichloroacetic acid from vessel 15 is added to the test and control samples in tubes 41. Vacuum pump 51 is then operated to create a negative pressure in the lower conical portions of the polyethylene tubes and thereby filter the mixture so as to deposit the precipitated bacteria on filter 44 of each tube. The filter is then washed with the washing solution in vessel 16.

Rotating transfer armlift 60 removes tubes 41, now containing washed bacteria freed of liquid culture medium, from programmable turntable 40 and delivers them to conveyor 71 where they are placed into scintillation vials 70. The samples then receive a dose of scintillation fluid from dispenser 75, and conveyor 71 conveys the resulting samples to radiation counter 77. The measured radioactivities of the test and control samples are then compared, and the difference, if any, is determined.

The following example is intended to illustrate the practice of the present invention, but not to limit the invention.

EXAMPLE

Isolated colonies of speciated bacteria were suspended in trypticase soy broth (TSB) to yield an optical density of 0.030/ml at 700 nm, corresponding to $0.5 \times 10^8$ cells per ml close to the cell concentration of a 0.5 McFarland standard. From this bacterial suspension, 100 microliter aliquots were pipetted into tubes containing 1 ml of TSB (controls) or TSB containing increasing concentrations of a variety of antibiotics that are routinely employed for susceptibility determinations. The control and antibiotic-containing cultures were incubated for varying intervals, and 15 minutes prior to each interval, the respective control and experimental cultures received 1 $\mu$Ci of 3H-thymidine having a specific activity of 22.4 Ci/mmol. The cultures were terminated at the end of the designated culture interval by the addition of ice cold 10 percent trichloroacetic acid. The thus-formed precipitates were collected with the aid of millipore filters and then washed with three volumes of trichloroacetic acid. The filters with collected precipitates were then dried and transferred to scintillation vials containing Beckman's Scintillant, and the amount of radioactivity was determined with the aid of a Beckman Scintillation counter. All of the cultures were performed at least in triplicate. The counts per minute (CPM) of each culture did not deviate by more than ±5 percent from the average CPM of the triplicate set. Corrections for quenching, etc., were routinely performed.

The general procedure outlined above was applied to six strains of *E. coli*, eight strains of *S. aureus*, six strains of *P. mirabilis*, five strains of Klebsiella sp. and six strains of Enterococci sp. The incubation times for the various species were set as the time required to permit incorporation of 50,000 counts per minute 3H-thymidine during a 15 minute pulse period, in the absence of antibiotic, and were determined to be 1 hour for *E. coli*, 2 hours for Klebsiella sp. and *S. aureus*, and 2.5 hours for *P. mirabilis* and Enterococci sp.

The data obtained from these experiments are summarized in Tables I–VII, below:

TABLE I

Effects of Multiple MIC Levels of Antibiotics on the Incorporation of 3H—Thymidine by 6 Strains of Susceptible* E. coli. Incubated for 1 hour.
AVERAGE % INHIBITION ± S.D.

| Antibiotic | ug/ml 1 × MIC | 1 × MIC | 5 × MIC | 10 × MIC | 20 × MIC | 50 × MIC | 100 × MIC |
|---|---|---|---|---|---|---|---|
| Ampicillin | 6.2 | 6.4 ± 4.1 | 12.8 ± 8.3 | 18.8 ± 9.4 | 33.0 ± 13.5 | 72.1 ± 31.1 | 93.4 ± 28.2 |
| Carbenicillin | 6.0 | 3.2 ± 0.6 | 5.8 ± 1.1 | 7.0 ± 1.5 | 20.8 ± 13.5 | 26.8 ± 17.1 | 34.9 ± 18.0 |
| Cefamandole | 0.5 | 5.1 ± 0.8 | 9.8 ± 1.2 | 12.1 ± 5.4 | 16.8 ± 8.1 | 39.1 ± 15.9 | 44.8 ± 12.0 |
| Chloramphenicol | 5.0 | 90.4 ± 1.2 | 92.8 ± 1.2 | 93.6 ± 1.6 | 94.4 ± 1.7 | 99 | 99 |
| Colistin | 3.0 | 8.2 ± 11.2 | 93.4 ± 4.9 | 94.6 ± 4.2 | 96.6 ± 1.4 | 99 | 99 |
| Gentamicin | 1.0 | 14.2 ± 10.1 | 34.6 ± 17.2 | 64.2 ± 16.7 | 86.0 ± 27.7 | 99 | 99 |
| Kanamycin | 4.0 | 10.0 ± 7.1 | 46.0 ± 15.7 | 67.2 ± 13.1 | 85.8 ± 5.3 | 99 | 99 |
| Keflin | 5.0 | 0 | 7.0 ± 3.1 | 14.0 ± 8.3 | 31.8 ± 11.0 | 49.4 ± 13.9 | 57.3 ± 14.6 |
| Nalidixic Acid | 5.0 | 95.5 ± 0.8 | 95.5 ± 0.7 | 96.5 ± 0.4 | 99 | 99 | 99 |
| Tetracycline | 5.0 | 78.2 ± 6.1 | 91.6 ± 0.4 | 93.0 ± 0.4 | 93.8 ± 0.2 | 99 | 99 |
| Tobramycin | 1.0 | 14.2 ± 10.1 | 34.6 ± 17.2 | 64.2 ± 16.7 | 86.0 ± 27.7 | 99 | 99 |

*Does not include strain K-12.

TABLE II

Effects of Multiple MIC Levels on the Incorporation of 3H—Thymidine by 6 Strains of E. coli. Incubated for 2.5 hours.
AVERAGE % INHIBITION ± S.D.

| Antibiotic | 1 × MIC | 5 × MIC | 10 × MIC | 20 × MIC | 50 × MIC | 100 × MIC |
|---|---|---|---|---|---|---|
| Ampicillin | 74.4 ± 8.1 | 91.0 ± 7.7 | 96.0 ± 7.0 | 99 | 99 | 99 |
| Carbenicillin | 8.9 ± 12.0 | 14.9 ± 18.4 | 28.4 ± 19.0 | 99 | 99 | 99 |
| Cefamandole | 52.8 ± 8.9 | 55.8 ± 8.7 | 90.0 ± 3.1 | 90.4 ± 2.4 | 93.6 ± 2.6 | 99 |
| Keflin | 31.6 ± 13.9 | 69.1 ± 10.5 | 75.8 ± 8.1 | 99 | 99 | |

TABLE III

Effects of Multiple MIC Levels of Antibiotics on the Incorporation of 3H—Thymidine by 6 Strains of P. mirabilis. Incubated for 2½ hours.
AVERAGE % INHIBITION ± S.D.

| Antibiotics | ug/ml 1 × MIC | 1 × MIC | 5 × MIC | 10 × MIC | 20 × MIC | 50 × MIC | 100 × MIC |
|---|---|---|---|---|---|---|---|
| Ampicillin | 20.0 | 53.6 ± 13.1 | 80.4 ± 7.8 | 89.0 ± 2.4 | 91.0 ± 1.8 | 99 | 99 |
| Carbenicillin | 25.0 | 25.6 ± 22.3 | 46.6 ± 22.8 | 54.8 ± 20.8 | 70.4 ± 15.8 | 92.4 ± 2.7 | 99 |
| Chloramphenicol | 20.0 | 94.8 ± 3.3 | 94.8 ± 2.8 | 99 | 99 | 99 | 99 |
| Gentamicin | 1.2 | 69.2 ± 8.3 | 92.4 ± 3.7 | 94.6 ± 3.7 | 99 | 99 | 99 |
| Kanamycin | 10.0 | 82.6 ± 11.5 | 89.4 ± 9.3 | 91.8 ± 4.7 | 99 | 99 | 99 |
| Keflin | 20.0 | 89.2 ± 2.2 | 90.8 ± 2.0 | 91.0 ± 1.7 | 99 | 99 | 99 |
| Nalidixic Acid | 50.0 | 92.8 ± 4.5 | 99 | 99 | 99 | 99 | 99 |
| Tetracycline | 10.0 | 61.4 ± 11.3 | 91.2 ± 10.9 | 91.6 ± 4.8 | 99 | 99 | 99 |
| Tobramycin | 4.0 | 82.2 ± 11.7 | 92.2 ± 4.4 | 94.1 ± 4.5 | 99 | 99 | 99 |

TABLE IV

Effects of Multiple MIC Levels of Antibiotics on the Incorporation of 3H—Thymidine by 5 Strains of Klebsiella sp. Incubated for 2 hours.
AVERAGE % INHIBITION ± S.D.

| Antibiotic | ug/ml 1 × MIC | 1 × MIC | 5 × MIC | 10 × MIC | 20 × MIC | 50 × MIC | 100 × MIC |
|---|---|---|---|---|---|---|---|
| Ampicillin | 50.0 | 8.0 ± 6.9 | 8.1 ± 7.4 | 8.1 ± 7.4 | 15.8 ± 8.2 | 60.4 ± 8.9 | 76.6 ± 5.1 |
| Chloramphenicol | 20.0 | 79.6 ± 4.6 | 79.0 ± 4.3 | 79.8 ± 4.2 | 82.4 ± 3.1 | 85.0 ± 2.3 | 85.6 ± 2.4 |
| Colistin | 6.2 | 77.8 ± 4.1 | 79.8 ± 3.6 | 79.2 ± 3.7 | 78.2 ± 4.1 | 88.4 ± 2.8 | 83.0 ± 3.8 |
| Gentamicin | 2.0 | 77.6 ± 4.1 | 78.4 ± 6.1 | 79.2 ± 5.8 | 80.6 ± 4.3 | 80.7 ± 4.0 | 81.2 ± 3.1 |
| Kanamycin | 10.0 | 71.6 ± 6.8 | 79.8 ± 3.7 | 79.8 ± 4.5 | 81.6 ± 4.1 | 79.4 ± 3.5 | 80.4 ± 3.8 |
| Keflin | 20.0 | 8.0 ± 7.1 | 77.6 ± 3.8 | 79.4 ± 3.0 | 78.8 ± 4.0 | 80.1 ± 4.1 | 81.0 ± 2.8 |
| Nalidixic Acid | 50.0 | 81.6 ± 3.9 | 79.2 ± 2.9 | 80.0 ± 3.0 | 80.8 ± 3.5 | 81.2 ± 2.5 | 81.4 ± 3.1 |
| Tetracycline | 10.0 | 75.2 ± 5.8 | 78.6 ± 2.2 | 80.2 ± 1.7 | 80.6 ± 4.2 | 80.8 ± 5.2 | 83.2 ± 3.9 |

TABLE V

Effects of Multiple MIC Levels of Antibiotics on the Incorporation of 3H—Thymidine by 8 Strains of S. aureus. Incubated for 2 hours.
AVERAGE % INHIBITION ± S.D.

| Antibiotic | ug/ml 1 × MIC | 1 × MIC | 5 × MIC | 10 × MIC | 20 × MIC | 50 × MIC | 100 × MIC |
|---|---|---|---|---|---|---|---|
| Ampicillin | 0.3 | 22.5 ± 21.4 | 64.0 ± 33.9 | 79.0 ± 22.3 | 83.6 ± 18.0 | 91.3 ± 10.3 | 94.5 ± 6.5 |

TABLE V-continued

Effects of Multiple MIC Levels of Antibiotics on
the Incorporation of 3H—Thymidine by 8 Strains of
S. aureus. Incubated for 2 hours.
AVERAGE % INHIBITION ± S.D.

| Antibiotic | ug/ml 1 × MIC | 1 × MIC | 5 × MIC | 10 × MIC | 20 × MIC | 50 × MIC | 100 × MIC |
|---|---|---|---|---|---|---|---|
| Clindamycin | 0.2 | 98.1 ± 0.6 | 99 | 99 | 99 | 99 | 99 |
| Chloramphenicol | 12.5 | 97.3 ± 1.1 | 99 | 99 | 99 | 99 | 99 |
| Gentamicin | 0.8 | 96.4 ± 2.2 | 97.5 ± 1.3 | 97.8 ± 0.8 | 99 | 99 | 99 |
| Kanamycin | 2.5 | 75.4 ± 13.5 | 97.0 ± 1.3 | 99 | 99 | 99 | 99 |
| Keflin | 0.2 | 25.4 ± 21.1 | 94.8 ± 3.2 | 95.3 ± 3.1 | 99 | 99 | 99 |
| Oxacillin | 0.32 | 4.4 ± 7.2 | 82.1 ± 21.7 | 96.3 ± 3.2 | 97.6 ± 1.2 | 97.8 ± 0.8 | 99 |
| Tetracycline | 0.1 | 25.0 ± 17.0 | 57.5 ± 3.8 | 65.6 ± 3.8 | 78.4 ± 3.5 | 78.6 ± 3.5 | 78.9 ± 3.5 |
| Tobramycin | 0.8 | 95.0 ± 4.7 | 96.1 ± 3.4 | 97.1 ± 1.7 | 97.6 ± 1.2 | 97.9 ± 0.9 | 99 |

TABLE VI

Effects of Multiple MIC Levels of Antibiotics on
the Incorporation of 3H—Thymidine by 6 Strains of
Enterococci sp. Incubated for 2.5 hours.
AVERAGE % INHIBITION ± S.D.

| Antibiotic | ug/ml 1 × MIC | 1 × MIC | 5 × MIC | 10 × MIC | 20 × MIC | 50 × MIC | 100 × MIC |
|---|---|---|---|---|---|---|---|
| Ampicillin | 1.6 | 96.6 ± 6.3 | 96.5 ± 5.6 | 99 | 99 | 99 | 99 |
| Chloramphenicol | 50.0 | 95.7 ± 7.5 | 99 | 99 | 99 | 99 | 99 |
| Erythromycin | 2.0 | 99 | 99 | 99 | 99 | 99 | 99 |
| Gentamicin | 12.5 | 83.2 ± 13.7 | 99 | 99 | 99 | 99 | 99 |

TABLE VII

Determination of E. coli Antibiotic
Susceptibility by the 3H—Thymidine
Method: Comparison to the Results
Obtained by Kirby Bauer.

| | 3H—Thymidine | | Kirby Bauer | | % |
|---|---|---|---|---|---|
| | Sensitive | Resistant | Sensitive | Resistant | Agreement |
| Ampicillin | 11 | 7 | 11 | 7 | 100% |
| Carbenicillin | 12 | 6 | 12 | 6 | 100% |
| Cefamandole | 17 | 1 | 17 | 1 | 100% |
| Keflin | 18 | 0 | 18 | 0 | 100% |
| Gentamicin | 18 | 0 | 18 | 0 | 100% |
| Chloramphenicol | 17 | 1 | 17 | 1 | 100% |
| Tobramycin | 18 | 0 | 18 | 0 | 100% |
| Amikacin | 18 | 0 | 18 | 0 | 100% |
| Kanamycin | 15 | 3 | 17 | 1 | 89% |
| Colistin | 18 | 0 | 18 | 0 | 100% |
| Nalidixic Acid | 14 | 0 | 14 | 0 | 100% |

Note:
% Agreement is determined by direct comparison of the results of the two methods for each specimen tested.

Although the invention has been described in terms of specific embodiments and applications, it is to be understood that persons skilled in the pertinent art, in light of this teaching, can produce additional embodiments without departing from the scope of the invention. Accordingly, the drawings and descriptions in this disclosure are merely illustrative of the principles of the invention, and should not be construed to limit the scope thereof.

What is claimed is:

1. A method for ascertaining the effect of a chemical on bacteria comprising the steps of:
   (1) dividing a specimen of bacteria into a test sample and a control sample;
   (2) culturing said test sample in the presence of a chemical for a first period of time;
   (3) culturing said control sample in the absence of said chemical for the same first period of time;
   (4) adding a radioactively-labelled nucleotide, wherein said nucleotide is selected from the group consisting of thymidine and thymidine analogs, to said test and control samples at a predetermined period of time after the beginning of, but before the expiration of said first period of time;
   (5) determining the uptake of radioactively-labelled nucleotide by said test and control samples; and
   (6) comparing the respective uptakes of radioactively-labelled nucleotide by said control and test samples.

2. A method according to claim 1 wherein said radiactively-labelled nucleotide is radioactively-labelled thymidine.

3. A method according to claim 2 wherein said radioactively-labelled thymidine is labelled with an isotope which emits beta-rays.

4. A method according to claim 2 wherein said radioactively-labelled thymidine is tritiated thymidine.

5. A method according to claim 4 wherein said labelled thymidine has a specific activity of at least 20 Curies per millimole.

6. A method according to claim 2 wherein said radioactively-labelled thymidine is $C^{14}$-labelled thymidine.

7. A method according to claim 1 wherein said chemical is an antibiotic.

8. A method according to claim 1 wherein the species of an unknown bacteria is determined by subdividing said test sample into a plurality of subpopulations, incubating said subpopulations in the presence of a plurality of different chemicals, and ascertaining the pattern of effects of said chemicals on the uptake of said radioactively-labelled nucleotide by said test subpopulations.

9. A method for ascertaining the effect of a chemical on bacteria according to claim 1 wherein said first period of time is sufficient to obtain detectable growth.

10. A method for ascertaining the effect of a chemical on bacteria according to claim 1 wherein said specimen of bacteria has a cell concentration of at least about $10^4$ cells per milliliter.

11. A method for ascertaining the effect of a chemical on bacteria according to claim 10 wherein said specimen of bacteria has a cell concentration of from about $10^5$ to about $10^{10}$ cells per milliliter.

12. A method of ascertaining the effect of a chemical on bacteria according to claim 1 wherein said predetermined period of time after the beginning of, but before the expiration of said first period of time, begins between about 25 minutes to about 5 minutes before said expiration of said first period of time.

13. A method according to claim 7 wherein said bacteria is disease causing and said nucleotide is radioactively-labelled thymidine.

14. A method according to claim 7 wherein said bacteria is disease causing and said nucleotide is a radioactively-labelled thymidine analog.

15. A method according to claim 1 wherein said test and said control samples are cultured in a complete liquid culture medium for said first period of time.

16. A method according to claim 1 wherein said radioactively-labelled nucleotide is added to said test and said control samples after said chemical has had a significant effect on said bacteria in said test sample.

17. A method for rapidly determining the susceptibility of pathogenic bacteria to antibiotics comprising the steps of:
   (1) preparing an aqueous suspension of pathogenic bacteria;
   (2) adjusting the concentration of said pathogenic bacterial suspension to between about $10^5$ to about $10^{10}$ bacteria cells/ml;
   (3) dividing said cell concentration adjusted pathogenic bacterial suspension into to at least two samples;
   (4) preparing a first complete liquid culture medium containing a known concentration of an antibiotic;
   (5) preparing a second complete liquid culture medium without said antibiotic;
   (6) adding a first sample of said pathogenic bacterial suspension to a volume of said first complete liquid culture medium containing said antibiotic to result in a cell concentration between $10^4$ to $10^9$ cells/ml in said first complete liquid culture medium, thereby forming a test sample;
   (7) adding a second sample of said pathogenic bacterial suspension to a volume of said second complete liquid culture medium without said antibiotic to result in a cell concentration between $10^4$ to $10^9$ cells/ml in said second complete liquid culture medium, thereby forming a control sample;
   (8) culturing said test and control samples for a period of time of at least about $\frac{1}{2}$ hour but not longer than $2\frac{1}{2}$ hours;
   (9) adding tritiated thymidine with a specific activity in excess of 6 Ci/mmole to said test and control samples about 15 minutes before the expiration of said culturing time period;
   (10) analyzing said test and control samples after said culturing to determine the thymidine uptake for each sample; and
   (11) comparing the results of said analyses.

18. A method according to claim 17 wherein steps (1)–(11) are repeated three times.

19. A method according to claim 9 wherein said first period of time sufficient to obtain detectable growth is generally at least one-half hour, but generally not greater than two and one-half hours.

20. A method according to claim 7 which further comprises:
   (1) dividing said test sample into a plurality of subsamples; and
   (2) culturing said test subsamples in the presence of a plurality of concentrations of said antibiotic.

* * * * *

UNITED STATES PATENT AND TRADEMARK OFFICE
CERTIFICATE OF CORRECTION

PATENT NO. : 4,604,351

DATED : August 5, 1986

INVENTOR(S) : Leonard Amaral

It is certified that error appears in the above-identified patent and that said Letters Patent is hereby corrected as shown below:

Column 1, line 5, "554,159" should read -- 554,149 --.

Column 2, line 17 "and" should read -- are --.

Column 2, line 18, "bacteria; and consequently" should read -- bacteria; consequently. --.

Column 2, line 29, "solely to" should read -- solely for --.

Column 2, line 32, "susceptability" should read -- susceptibility --.

Column 3, line 18, "such" should read -- said --.

Column 3, line 19, "subpopulation" should read -- subpopulations --.

Column 6, line 61, "the the respective" should read -- the respective --.

Column 11, line 19, "preferable" should read -- preferably --.

Column 12, line 62, "minute 3H" should read -- minute of 3H --.

UNITED STATES PATENT AND TRADEMARK OFFICE
CERTIFICATE OF CORRECTION

PATENT NO. : 4,604,351

DATED : August 5, 1986

INVENTOR(S) : Leonard Amaral

It is certified that error appears in the above-identified patent and that said Letters Patent is hereby corrected as shown below:

Column 17, line 31, "into to at" should read -- into at --.

Signed and Sealed this

Thirty-first Day of March, 1987

Attest:

DONALD J. QUIGG

Attesting Officer     Commissioner of Patents and Trademarks